(12) United States Patent
Belleville et al.

(10) Patent No.: US 8,936,401 B2
(45) Date of Patent: Jan. 20, 2015

(54) METHOD FOR DISPOSABLE GUIDEWIRE OPTICAL CONNECTION

(76) Inventors: Claude Belleville, Québec (CA); Sébastien Lalancette, St-Augustin-de-Desmaures (CA); Alain Proulx, St-Pierre-de-la-Rivière-du-Sud (CA)

( * ) Notice: Subject to any disclaimer, the term of this patent is extended or adjusted under 35 U.S.C. 154(b) by 83 days.

(21) Appl. No.: 13/598,596

(22) Filed: Aug. 29, 2012

(65) Prior Publication Data
US 2013/0051731 A1 Feb. 28, 2013

Related U.S. Application Data

(60) Provisional application No. 62/529,029, filed on Aug. 30, 2011.

(51) Int. Cl.
*G02B 6/36* (2006.01)
*G02B 6/38* (2006.01)
*A61B 5/0215* (2006.01)
*G02B 6/44* (2006.01)

(52) U.S. Cl.
CPC .............. *G02B 6/38* (2013.01); *G02B 6/3861* (2013.01); *G02B 6/3873* (2013.01); *G02B 6/389* (2013.01); *A61B 5/02154* (2013.01); *G02B 6/381* (2013.01); *G02B 6/3898* (2013.01); *G02B 6/4402* (2013.01); *G02B 6/4415* (2013.01)
USPC .................. 385/80; 385/76; 385/77; 385/78; 385/86

(58) Field of Classification Search
CPC .. G02B 6/3821; G02B 6/3834; G02B 6/3861; G02B 6/3877
USPC .......................................................... 385/80
See application file for complete search history.

(56) References Cited

U.S. PATENT DOCUMENTS

| | | | |
|---|---|---|---|
| 4,941,473 A | 7/1990 | Tenerz et al. | |
| 4,958,642 A | 9/1990 | Christian et al. | |
| 4,961,433 A | 10/1990 | Christian et al. | |
| 5,125,058 A | 6/1992 | Tenerz et al. | |
| 5,178,159 A | 1/1993 | Christian et al. | |
| 5,187,761 A * | 2/1993 | Mehadji et al. | 385/76 |
| 5,240,437 A | 8/1993 | Christian et al. | |
| 5,348,481 A | 9/1994 | Ortiz et al. | |
| 5,358,409 A | 10/1994 | Obara | |
| 5,413,508 A | 5/1995 | Obara | |
| 5,601,087 A | 2/1997 | Gunderson et al. | |

(Continued)

FOREIGN PATENT DOCUMENTS

EP 0943110 3/2005

OTHER PUBLICATIONS

International Searching Authority, International Search Report, Dec. 13, 2012.

*Primary Examiner* — Ryan Lepisto
(74) *Attorney, Agent, or Firm* — Benoît & Côté Inc.

(57) ABSTRACT

A method for terminating a first optical fiber within a proximal portion of a guidewire tubing. The guidewire tubing has an outside diameter defined as having a tolerance of ±0.001" or less. The method comprises the step of centering the first optical fiber within the guidewire tubing. A female optical receiving device used to receive an optical guidewire and connect guidewire internal optical fiber to an external relaying optical cable is also provided.

9 Claims, 7 Drawing Sheets

(56) References Cited

U.S. PATENT DOCUMENTS

| | | |
|---|---|---|
| 5,785,729 A * | 7/1998 | Yokokawa et al. ............ 65/385 |
| 6,112,598 A | 9/2000 | Tenerz et al. |
| 6,134,003 A | 10/2000 | Tearney et al. |
| 6,167,763 B1 | 1/2001 | Tenerz et al. |
| 6,196,980 B1 | 3/2001 | Akerfeldt et al. |
| 6,428,336 B1 | 8/2002 | Akerfeldt |
| 6,445,939 B1 | 9/2002 | Swanson et al. |
| 6,565,514 B2 | 5/2003 | Svanerudh et al. |
| 6,687,434 B2 | 2/2004 | Ishikawa |
| 6,714,809 B2 | 3/2004 | Lee et al. |
| 7,245,789 B2 | 7/2007 | Bates et al. |
| 7,252,677 B2 | 8/2007 | Burwell et al. |
| 7,259,862 B2 | 8/2007 | Duplain |
| 7,274,956 B2 | 9/2007 | Mott et al. |
| 7,349,618 B2 | 3/2008 | Nielsen et al. |
| 7,532,920 B1 | 5/2009 | Ainsworth et al. |
| 7,689,071 B2 | 3/2010 | Belleville et al. |
| 7,717,624 B2 | 5/2010 | Carlin et al. |
| 7,736,301 B1 | 6/2010 | Webler et al. |
| 7,879,067 B2 | 2/2011 | Galdonik et al. |
| 2007/0196053 A1 | 8/2007 | Kewitsch |
| 2010/0256527 A1 | 10/2010 | Lippert et al. |

\* cited by examiner

METHOD FOR DISPOSABLE GUIDEWIRE OPTICAL CONNECTION

CROSS-REFERENCE TO RELATED APPLICATION

This application claims priority from U.S. patent application 61/529,029 filed Aug. 30, 2011, the specification of which is hereby incorporated herein by reference in its entirety.

FIELD

The subject matter disclosed generally relates to guidewires for minimally invasive medical use. More specifically, it relates to methods and devices for terminating optical fibers within guidewires.

BACKGROUND

The use of pressure measurement guidewires has been in existence for at least the last 10 years. These pressure guidewires are most commonly used to measure the pressure distal to a lesion (stenosis), most commonly in the coronary vasculature. By calculating the ratio between the measured pressure distal to the lesion and some point more proximal, most commonly in the ascending aorta or the coronary tree root, the fractional flow reserve (FFR) is obtained. The FFR is now commonly used to assess the significance of lesion stenosis and thereby to inform the physician as to the most appropriate treatment strategy.

Current devices use piezo-electric pressure transducing elements mounted into a guidewire for measuring blood pressure distal to stenosis that intervene in the calculation of the FFR value. Piezo-electric transducers however suffer from lack of stability as a result of moisture induced sensor drift. Optical pressure element as described in U.S. Pat. No. 7,689,071 do not suffer from such adverse effect and they are better suited for FFR measurement such as for pressure guidewire described in U.S. patent application Ser. No. 13/389,319.

Pressure guidewires also must allow easy disconnection and reconnection of the guidewire to a pressure analyzer. Pressure guidewires involve the measurement of distal blood pressure, followed by the insertion of other interventional medical devices such as Percutaneous Transluminal Coronary Angioplasty (PTCA) balloon catheter over the guidewire for stenting in case of significant lesion. It is however desirable to have the ability to reliably re-connect the guidewire to the pressure analyzer for post stenting FFR assessment, or for multi-vessel lesion assessment. Current electrical connectors such as those described in U.S. Pat. Nos. 4,958,642, 4,961,433, 5,178,159, 5,240,437, 5,358,409, 5,348,481, 5,413,508, 6,196,980, 6,428,336, 7,274,956 are suited for electrical connection. Although they have the ability to provide a reliable electrical connection in dry conditions, they are typically quite sensitive to conditions where the surface of the guidewire connector contacts are contaminated with blood residues after the removal of the interventional device such as PTCA balloon catheter.

A selection of prior art documents is described below. They are discussed for illustrative purposes only. These documents do not necessarily represent the closest prior art.

U.S. Pat. No. 5,125,058 provides a method for optically connecting a guidewire mounted device to a relaying cable. The method however relies on the accuracy of the internal diameter of the guidewire, which is difficult to achieve. The guidewire mounted optical fiber interface is recessed within the guidewire, making the fiber surface polishing a difficult task. The optical portion that is devoted to be inserted into the guidewire needs to be of very small diameter, making the connector very sensitive to mechanical damage.

U.S. Pat. No. 5,601,087 relies on the addition to the guidewire shaft of a proximal tubing portion, often called ferrule, with accurate outside diameter for alignment purpose. The addition of such proximal tubing portion adds extra production steps to the device and represents a challenging assembly process considering the presence of optical parts.

U.S. Pat. No. 6,445,939 also relies on the addition of a ferrule attached to the proximal end of the guidewire shaft. It is indeed very difficult and expensive to machine such a tinny precise ferrule, and to attach it to the proximal end of the guidewire shaft.

U.S. Pat. No. 7,736,301 also relies on the addition of a ferrule near the proximal end of the guidewire shaft. The ferrule is, in this case, not attached to the guidewire as it is desired to allow for rotational connection, hence further increasing the requirement on the diameter tolerance of the parts.

Hence, there is a need for an optical guidewire connector having the ability to reliably connect a guidewire mounted optical pressure sensor to an external pressure analyzer or a similar opto-electronic device; that is disposable, and hence that is easy to produce and is low in cost of material; and that is not sensitive to the presence of moisture or blood contamination.

SUMMARY

According to an embodiment, there is described a method for terminating a first optical fiber within a proximal portion of a guidewire tubing. The guidewire tubing has an outside diameter defined as having a tolerance of 0.001" or better. The method comprises centering the first optical fiber within the guidewire tubing.

According to an aspect, the method further comprises grinding, polishing, or etching the guidewire tubing to bring the outside diameter within a tolerance of ±0.001" or better.

According to an aspect, a gap exists between an outside diameter of the first optical fiber and an inside diameter of the guidewire tubing, the method further comprising slipping an overlay tubing over the optical fiber to fill the gap at least in part.

According to an aspect, the centering comprises centering the first optical fiber relative to the outside diameter of the guidewire tubing using an alignment centering tubing device, the method further comprising using an adhesive for securing the first optical fiber in the center of guidewire proximal portion.

According to an aspect, the alignment centering tubing device comprises a first ferrule having an inside diameter adapted to the outside diameter of the guidewire tubing, a second ferrule having an inside diameter adapted to an outside diameter of the first optical fiber, the method further comprising concentrically aligning the first ferrule and the second ferrule.

According to an aspect, the aligning the first ferrule and second ferrule comprises using a split sleeve over the first ferrule and second ferrule thereby holding both ferrules coaxially.

According to an aspect, a gap exists between an outside diameter of the first optical fiber and an inside diameter of the guidewire tubing, and wherein the centering further comprising slipping an overlay tubing over the optical fiber to fill the gap at least in part.

According to an aspect, the alignment centering tubing device comprises a first ferrule having an inside diameter adapted to the outside diameter of the guidewire tubing, a second ferrule having an inside diameter adapted to an outside diameter of an overlay tubing, the method further comprising concentrically aligning the first ferrule and the second ferrule.

According to another embodiment, there is described a method for connecting a first optical fiber within a proximal portion of a guidewire tubing, the method comprising: centering the first optical fiber within the proximal portion of the guidewire tubing; and connecting the first optical fiber to a female connector comprising a second optical fiber having a core diameter different from a core diameter of the first optical fiber.

According to an aspect, the method further comprises connecting the first optical fiber to a female connector comprising an alignment centering tubing device comprising a first ferrule having an inside diameter adapted to the outside diameter of the guidewire tubing, a second ferrule having an inside diameter adapted to an outside diameter of a second optical fiber for relaying an optical signal to an external signal conditioner unit, the method further comprising concentrically aligning the first ferrule and the second ferrule.

According to an aspect, the first ferrule and second ferrule are aligned with a split sleeve holding both ferrules coaxially.

According to another embodiment, there is described a female optical receiving device for connecting a first optical fiber to a second optical fiber, the first optical fiber being substantially centered within a proximal portion of a guidewire tubing, the female optical receiving device comprising a first ferrule having a longitudinal axis and an inside diameter adapted to an outside diameter of the guidewire tubing, a second ferrule having a longitudinal axis and an inside diameter adapted to an outside diameter of the second optical fiber, the longitudinal axis of the first ferrule being aligned with the longitudinal axis of the second ferrule.

According to an aspect, the device further comprises a split sleeve slipped and fixed over the first ferrule and the second ferrule simultaneously thereby aligning the longitudinal axis of the first ferrule and the longitudinal axis of the second ferrule.

According to an aspect, the second optical fiber has a core diameter different from a core diameter of the first optical fiber, the second optical fiber being fixed within the second ferrule.

According to another embodiment, there is described, an interface connector handle for connecting a first optical fiber to a second optical fiber, the first optical fiber being substantially centered within a proximal portion of a guidewire tubing, the second optical fiber being routed through and extending from an optical interface cable, the interface connector handle comprising a biasing assembly for urging the first optical fiber into contact with the second optical fiber.

According to an aspect, the handle further comprises a female optical receiving device at a distal end of the second optical fiber and wherein first optical fiber is for insertion in the female optical receiving device in order to contact the second optical fiber.

According to an aspect, the biasing assembly comprises a collet through which the guidewire tubing is pushed and held in place when the collet is in a closed position.

According to an aspect, the biasing assembly further comprises a biasing device and a connector cap through which the guidewire tubing is slid toward the female optical receiving device, the connector cap capable of movement in a direction, the biasing device exercising a counter force opposite the direction of movement of the connector cap, the counter force forcing the collet toward the closed position.

According to another embodiment, there is described a method for terminating a first optical fiber within a proximal portion of a guidewire tubing, the method comprising centering the first optical fiber relative to the outside diameter of the guidewire tubing using an alignment centering tubing device, the method further comprising using an adhesive for securing the first optical fiber in the center of guidewire proximal portion.

According to an aspect, the alignment centering tubing device comprises a first ferrule having an inside diameter adapted to the outside diameter of the guidewire tubing, a second ferrule having an inside diameter adapted to an outside diameter of the first optical fiber, the method further comprising concentrically aligning the first ferrule and the second ferrule.

According to an aspect, the aligning the first ferrule and second ferrule comprises using a split sleeve over the first ferrule and second ferrule thereby holding both ferrules coaxially.

BRIEF DESCRIPTION OF THE DRAWINGS

The accompanying drawings, which are included to provide a further understanding of the invention are incorporated and constitute a part of this specification, illustrate an exemplary embodiment of the invention that together with the description serve to explain the principles of the invention.

DETAILED DESCRIPTION

In the following description of the embodiments, references to accompanying drawings are by way of illustration of an example by which the invention may be practised. It will be understood that other embodiments may be made without departing from the scope of the invention disclosed.

Figure 1:
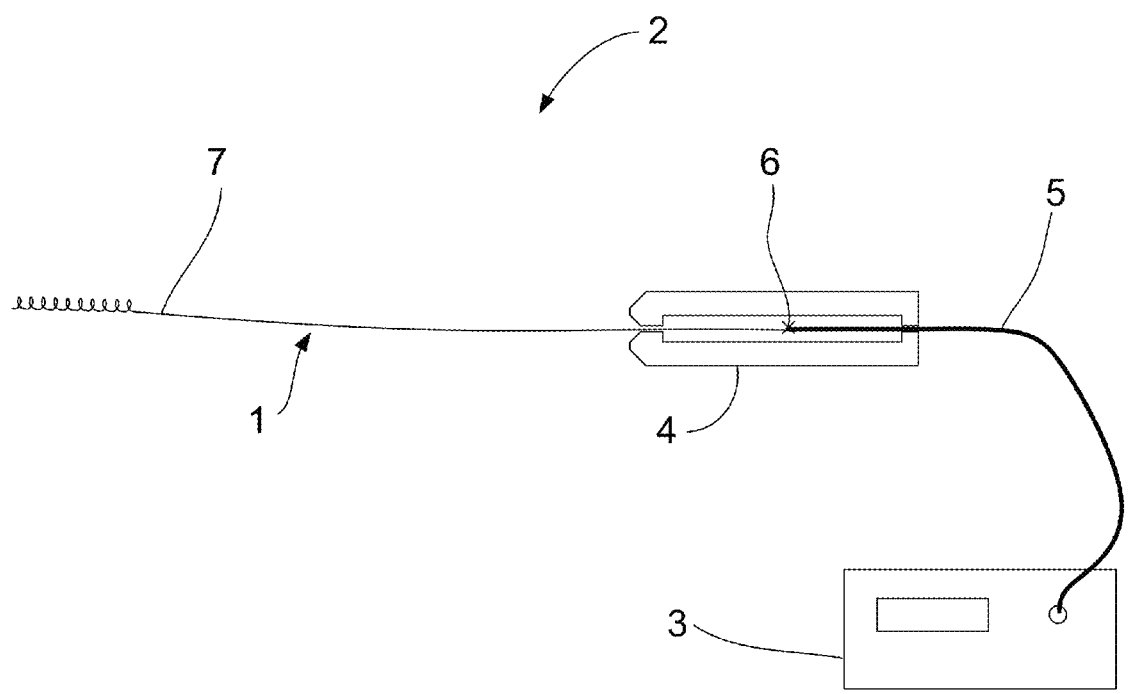
FIG. 1 is a schematic diagram of the guidewire assembly connection showing a cross-section of an interface cable handle according to an embodiment.

The system 2 for measuring FFR is shown in FIG. 1. It comprises a guidewire 1 instrumented with an optical pressure sensor 7 near the distal end (toward the patient). The guidewire 1 is therefore built with a hollow tubing (i.e., a guidewire tubing) for accommodating the optical fiber (not shown). The guidewire proximal end (toward the clinician) is terminated with a connectivity end for connecting to optical interface cable 5. The optical interface cable 5 is used to relay the optical signal from signal conditioner unit 3 (e.g., an optical analyzer) to guidewire mounted optical pressure sensor 7, and back to signal conditioner unit 3. Guidewire 1 comprises an internal optical fiber (not shown) that carries the light signal to the optical pressure sensor 7 and back to signal conditioner unit 3. In this respect, both optical fiber in the guidewire 1 and the optical fiber in the optical interface cable 5 need to be coaxially aligned and held in contact during use. The distal end of the optical interface cable 5 is terminated with optical alignment device 6 (also referred to herein as the female optical receiving device) that is embedded within the interface cable handle 4.

Figure 2:
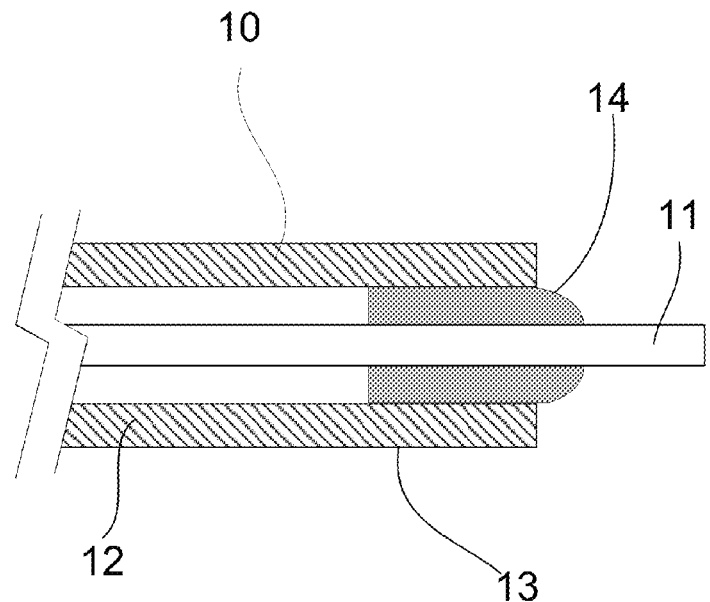
FIG. 2 is a schematic diagram showing a cross-section of the proximal end of the guidewire with its optical fiber protruding therefrom according to an embodiment.

FIG. 2 shows a first embodiment of the proximal portion 10 of the guidewire 1 such that after some further processing as detailed with reference to FIG. 3 herein below, it can be connectorized to an optical interface cable 5 (see FIG. 7a). Guidewire proximal portion outer diameter 13 of the guidewire 1 has an accurate and precise diameter.

The first optical fiber 11 can be aligned in the center of the guidewire tubing 12 with a positioning apparatus having the ability to mechanically position the first optical fiber 11 in the center of the guidewire 1, i.e., concentric with the end of the guidewire proximal portion 10. The position of the first optical fiber 11 relative to the guidewire tubing 12 is measured by methods such as those available from Beta LaserMike, Dayton, Ohio.

Figure 3:
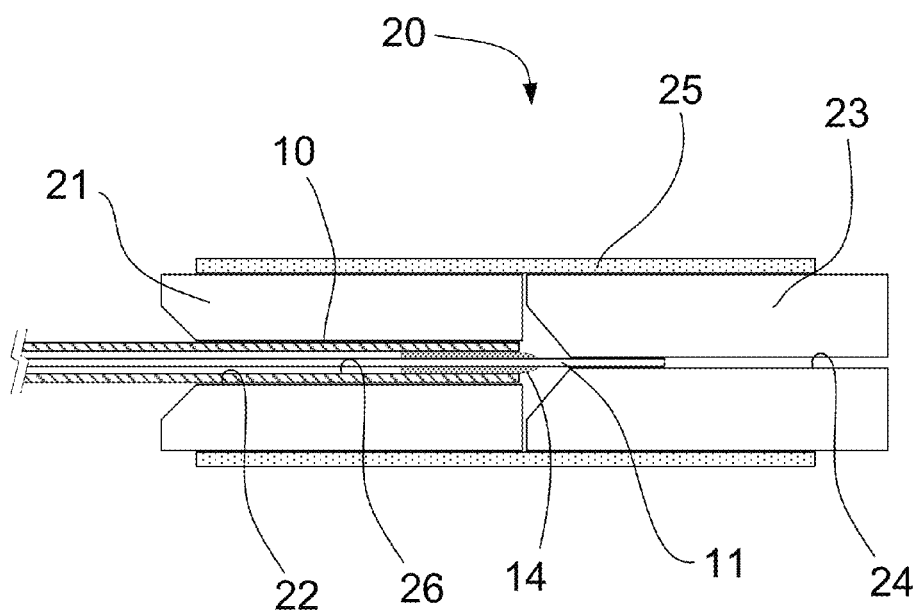
FIG. 3 is schematic diagram showing a cross-section of an alignment assembly device for aligning the optical fiber in the center of the proximal end of guidewire according to an embodiment.

The optical fiber alignment method shown in FIG. 3 is a preferred method because its compactness does not require a high level of mechanical stability for the assembly apparatus, while also being a self-alignment method. The alignment assembly device 20 (also known as an alignment centering tubing device) is made of a first alignment ferrule 21, tubing or similar device having a precise internal diameter 22 adapted to receive the guidewire proximal portion 10. By way of example, the first alignment ferrule 21 is preferably made with a commercial optical fiber alignment ferrule, either made of ceramic, zirconium, glass, stainless steel or other material providing adequate support and alignment accuracy. In the following, it is understood that ferrule is either a ferrule, a tubing or other similar device made of ceramic, zirconium, glass, stainless steel or other adequate material. Commercial ferrules for optical fibers are made with tolerances on eccentricity and hole diameter of the order of ±1 micron. A preferred outside diameter of such ferrules is typically of 1.25 mm, although it can be of other diameters such as 2.5 mm. The second alignment ferrule 23 is used to receive the first optical fiber 11 and it is therefore selected to have an internal diameter 24 that matches the diameter of the optical fiber cladding. Both ferrules are then coaxially aligned with the use of a split sleeve 25.

Proper centering of the first optical fiber 11 within the guidewire proximal portion 10 is therefore possible considering the guidewire proximal portion outer diameter 13 is accurate. The guidewire proximal portion 10 shall have an guidewire proximal portion outer diameter 13 with a tolerance better than ±0.001", and preferably it shall have a tolerance better than ±0.0005". One preferred method of obtaining a diameter with an accuracy of ±0.0005" or better is to grind the guidewire proximal portion 10 of the guidewire tubing 12 outer surface using a center-less grinder or other types of grinders known by those skilled in the art to be appropriate for this task. It is also obvious for those skilled in the art that other methods such as electro-etching can be used for the same purpose. The first optical fiber 11 is then aligned in the axial center of the guidewire tubing 12, and fixed in place using an adhesive 14.

Alignment assembly device 20 shown in FIG. 3 is therefore used to center the first optical fiber 11 in the guidewire tubing 12. The optical guidewire is prepared by letting the first optical fiber 11 protrude out of the guidewire tubing 12. The required amount of adhesive 14 is then provided to fill the gap between the first optical fiber 11 and the internal surface 26 of the guidewire proximal portion 10, and left uncured. The guidewire proximal portion 10 with protruding first optical fiber 11 is then inserted into the first alignment ferrule 21 and pushed such that the first optical fiber 11 enters into the second alignment ferrule 23. Depending on specific alignment assembly device 20, the guidewire proximal portion 10 can be pushed close to or in intimate contact with the second alignment ferrule 23, hence minimizing optical fiber misalignment that may be caused by the first optical fiber 11 bending outside second alignment ferrule 23. The adhesive 14 is then cured according to known adhesive curing methods.

An alternative method consists in inserting the guidewire proximal portion 10 within the first alignment ferrule 21 and pushed such that the first optical fiber 11 enters into the second alignment ferrule 23 with no adhesive yet. The required amount of adhesive 14 for filling the gap between the first optical fiber 11 and the internal surface 26 of the guidewire proximal portion 10 is then provided, followed by a curing step of the adhesive 14. This alternative method helps in preventing the adhesive 14 from also filling the gap between the guidewire proximal portion 10 and the internal surface of the first alignment ferrule 21, allowing an easy removal of the guidewire assembly after the adhesive 14 is cured.

Figure 4:
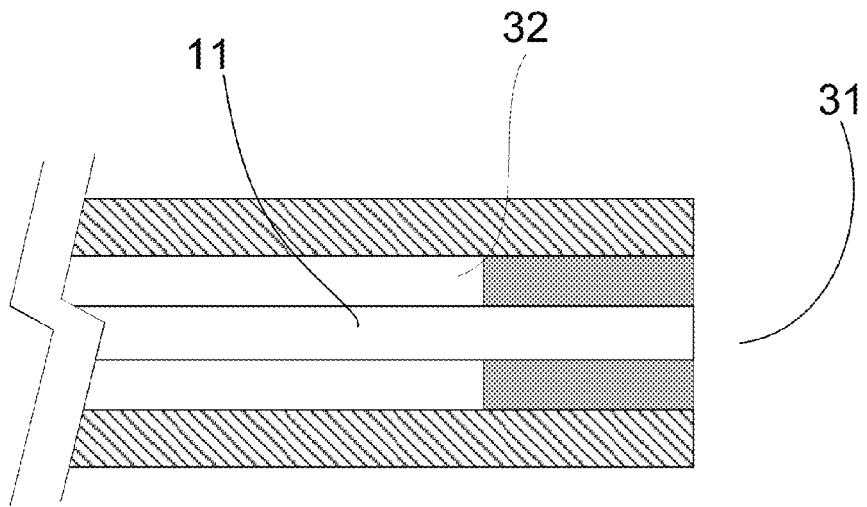
FIG. 4 is schematic diagram showing a cross-section of guidewire proximal end terminated to provide connectivity according to an embodiment.

Once the adhesive 14 is cured, the guidewire with centered first optical fiber 11 is retrieved from the alignment assembly device 20 to be terminated as shown in FIG. 4. The guidewire optical termination surface 31 of the guidewire is polished such that the first optical fiber 11 can be connected to the interface cable optical fiber (not shown here). Although the guidewire optical termination surface 31 can be polished on a hard surface, it is preferred to polish the guidewire proximal portion 10 on a soft polishing surface such that the optical fiber termination is provided with the ability to form a physical contact with the interface cable optical fiber.

The optical connectorization method shown in FIG. 4 is however not optimal. The relatively large amount of adhesive 14 used to fill the gap 32 between the first optical fiber 11 and the internal diameter of the guidewire tubing 12 makes such optical connection susceptible to optical fiber misalignment during assembly and over time. As the amount of adhesive 14 increases during assembly, the risk of having the adhesive 14 unevenly distributed increases, which in turn increases the risks of unevenly pulling the first optical fiber 11 off the axial center. In use, all adhesives have the tendency to swell over time, especially when in presence of moisture and with temperature change. A relatively large amount of adhesive 14 therefore makes the optical termination more unstable.

Figure 5:
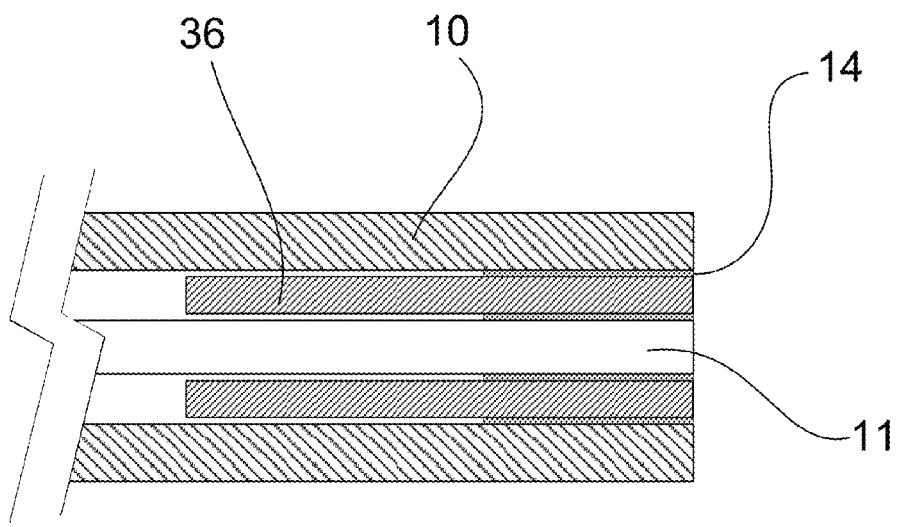
FIG. 5 is a schematic diagram showing a cross-section of guidewire proximal end terminated to provide connectivity according to another embodiment that comprises an overlay tubing.

The termination shown in FIG. 5 is a variation of the one shown in FIG. 4, where the gap between the first optical fiber 11 and the internal surface 26 of the guidewire proximal portion 10 is partially filled with an overlay tubing 36. In an embodiment, the overlay tubing 36 is selected to precisely match the first optical fiber 11. The amount of adhesive 14 holding the fiber in the center of the guidewire proximal portion 10 is significantly reduced, hence long term stability of the optical connection is assured.

The optical connection illustrated in FIG. 5 can be terminated using the same optical assembly device shown in FIG. 3. The overlay tubing 36 in this case would just barely extend further than the guidewire proximal portion 10 during assembly.

Figure 6A:
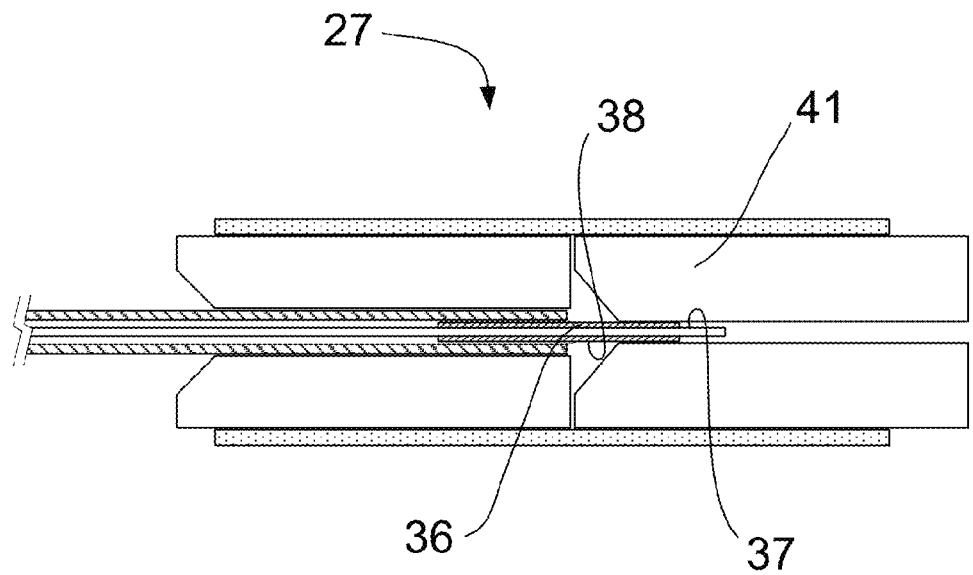
FIG. 6 is a schematic diagram showing a cross-section of an alignment assembly device for aligning the optical fiber with overlay tubing in the center of the proximal end of guidewire according to another embodiment.

For those cases where the overlay tubing 36 is very precise, it may however be desirable to use the alignment assembly device 27 shown in FIG. 6a, where the second alignment ferrule 41 has an internal diameter adapted to receive the overlay tubing 36. However, misalignment errors caused by tolerances of inner diameter 37 and outer diameter 38 of the overlay tubing 36 add up to the final coaxial positioning error of the first optical fiber 11, potentially leading to sub-optimal concentricity. It has been found that the optical fiber provides adequate stiffness for aligning concentrically with the guidewire when aligned with set-up and alignment method shown in FIG. 3. A preferred method consists in using an overlay tubing that does not precisely fit over the first optical fiber 11.

Figure 6B:
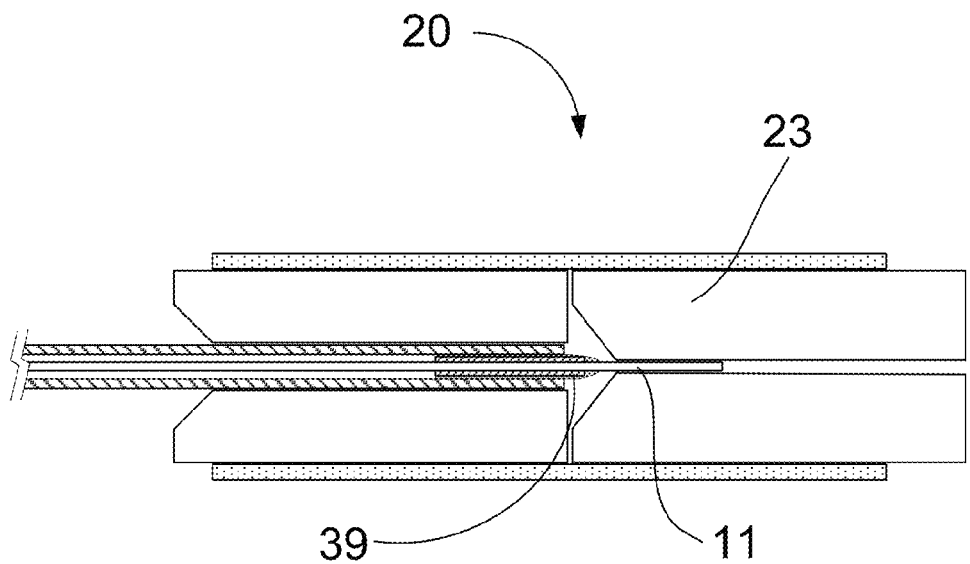

FIG. 6b illustrates such a preferred assembly method and alignment assembly device 20 using an overlay tube 39 that does not precisely fit over the first optical fiber 11. The concentric alignment of the first optical fiber 11 within the guidewire proximal portion 10 is assured by inserting the first optical fiber 11 in a second alignment ferrule 23 having an internal diameter matching the outside diameter of the first optical fiber 11, while the overlay tube 39 purpose is mainly for filling the gap 32 (shown in FIG. 4).

The above embodiments describe various methods and devices for making an optical connection at the proximal end of an optical guidewire. There is however also a need for a female part receiving the guidewire optical connection to provide an optical connection with the optical interface cable 5 for relaying the optical signal to a signal conditioner unit 3 (see FIG. 1).

Figure 7A:
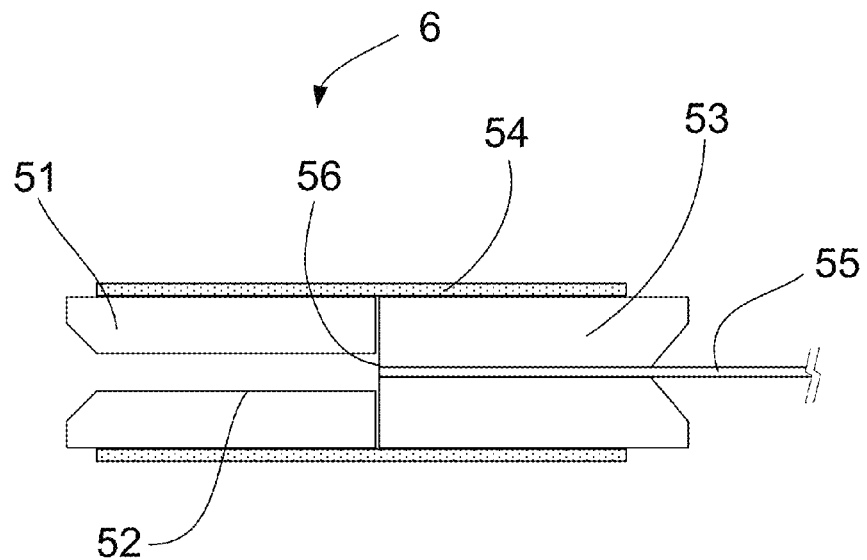
FIGS. 7a and 7b are schematic diagrams showing cross-sections of an optical female connectivity part used to receive a guidewire proximal end and aligning respective fibers together according to an embodiment.
Figure 7B:
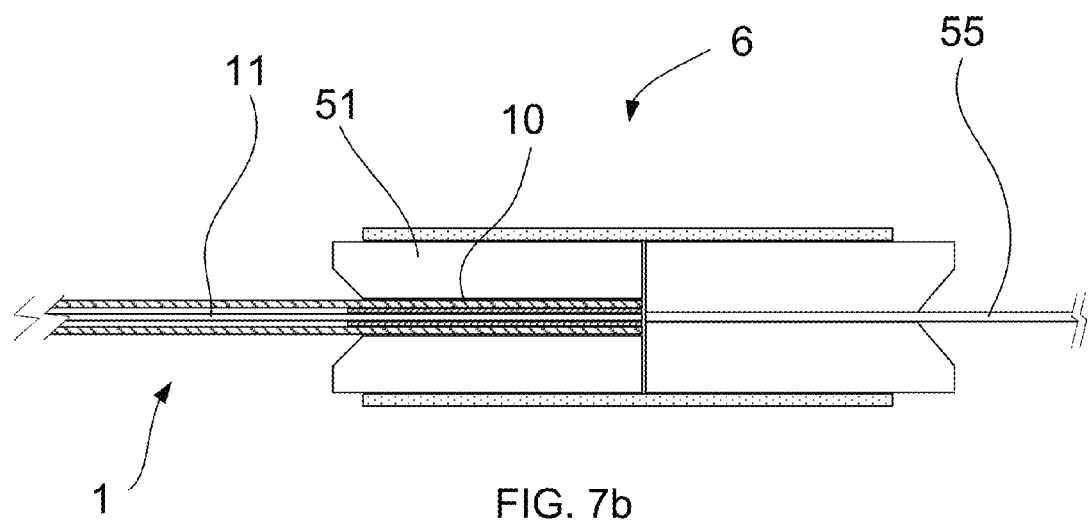

FIGS. 7a and 7b show the optical parts used to construct such a female optical receiving device 6. The female optical receiving device 6 is built in a way very similar to the alignment assembly device 20 shown in FIG. 3. The first ferrule 51 herein is also used to receive the guidewire 1, with the inner diameter 52 adapted to receive the guidewire proximal portion 10. First ferrule 51 and second ferrule 53 are aligned and held together using split sleeve 54. The second ferrule 53 is however selected to receive the second optical fiber 55 routed through the optical interface cable 5 (see FIGS. 1 and 8). By way of an example, the optical interface cable 5 comprises the second optical fiber 55 having a core diameter of 62.5 µm and a cladding diameter of 125 µm. In this case, the second ferrule 53 is selected with a diameter of 126 µm or 127 µm. The second optical fiber 55 is bonded inside the second ferrule 53 and polished so as to provide an adequate optical surface 56 compatible with the guidewire optical termination.

FIG. 7b shows the female optical receiving device 6 with the guidewire proximal portion 10 engaged within the first ferrule 51. The optical connection will take place with minimal losses provided that the first optical fiber 11 is coaxially aligned with the second optical fiber 55, and provided that the faces of both first optical fiber 11 and second optical fiber 55 are in intimate contact.

Figure 8:
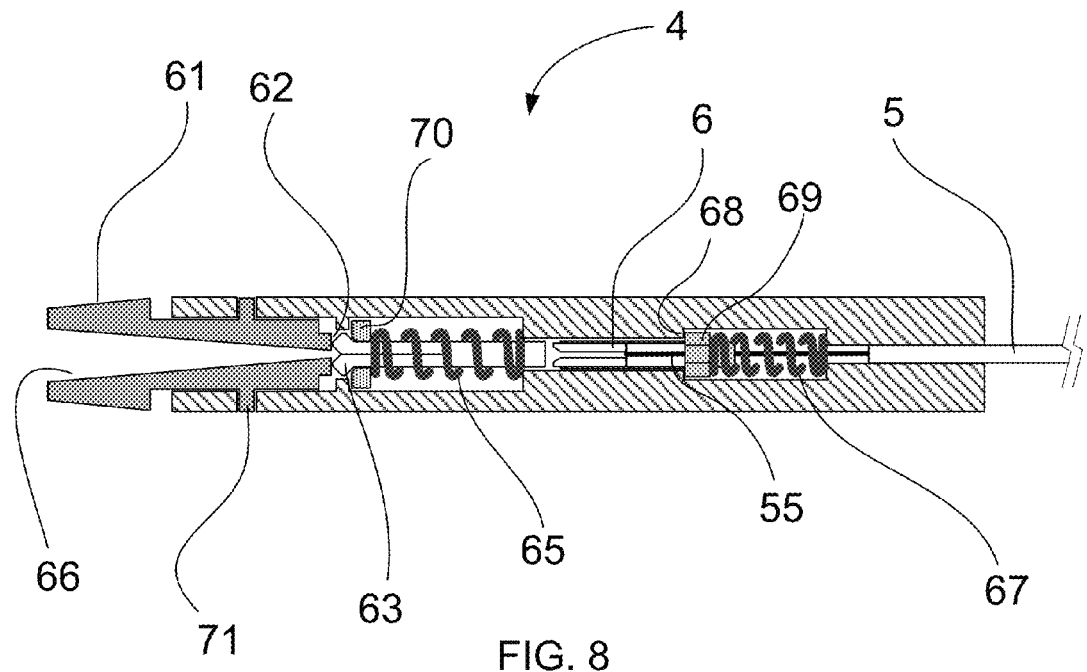
FIG. 8 is a schematic diagram showing a cross-section view of a handle which can be used in a method for holding female receiving optical parts at the end of an optical interface cable according to an embodiment.

FIG. 8 shows an interface connector handle 4 which can be used in a method for holding the female optical receiving device 6. A second optical fiber 55 is connected to the female optical receiving device 6 on one side, and runs through the optical interface cable 5 on the other side. The female optical receiving device 6 is held in the center of the interface connector handle 4 and pushed against a surface 68 with the help of a spring 67. The guidewire proximal portion 10 (see FIG. 7b) is inserted through the conical entrance 66 of the connector cap 61, it is pushed through the collet 63 then inside the female optical receiving device 6 such that the guidewire optical termination surface 31 (see FIG. 4) and the optical surface 56 (see FIG. 7a) of the second optical fiber 55 are in contact. The user can then tighten the connector cap 61. Connector cap proximal end 62 therefore pushes on collet 63 which results in closing such collet 63 by counter force exerted by spring 65 through seat 70. It is understood that spring 65 can be replaced by similar device such as rubber tube or other biasing device. The action of pushing the tightening collet 63 into seat 70 has the effect of closing the tightening collet 63 onto the guidewire proximal portion 10, firmly holding it in place.

According to an embodiment, the interface connector handle 4 comprises a biasing assembly (not number) for urging the first optical fiber 11 into contact with the second optical fiber 55. The biasing assembly may comprise collet 63 through which the guidewire 1 is pushed and held in place when the collet 63 is in a closed position. The biasing assembly may further comprise a biasing device (spring 65) and connector cap through which the guidewire tubing is slid toward the female optical receiving device, the connector cap 61 capable of movement in a direction. The biasing device exercises a counter force opposite the direction of movement of the connector cap 61 and the counter force forces the collet 63 toward the closed position.

One aspect of the method using interface connector handle 4 is to assure and maintain a good physical contact between both the optical interface of guidewire 1 and the optical interface of female optical receiving device 6. Physical contact is assured by the displacement of the guidewire proximal portion 10 provided upon tightening the connector cap 61. Upon tightening connector cap 61, collet 63 first closes and grips the guidewire proximal portion 10, forcing guidewire optical termination surface 31 (see FIG. 4) to push against the optical surface 56 of the second optical fiber 55 (see FIG. 7a). This action is illustrated in FIGS. 10a and 10b.

Figure 9:
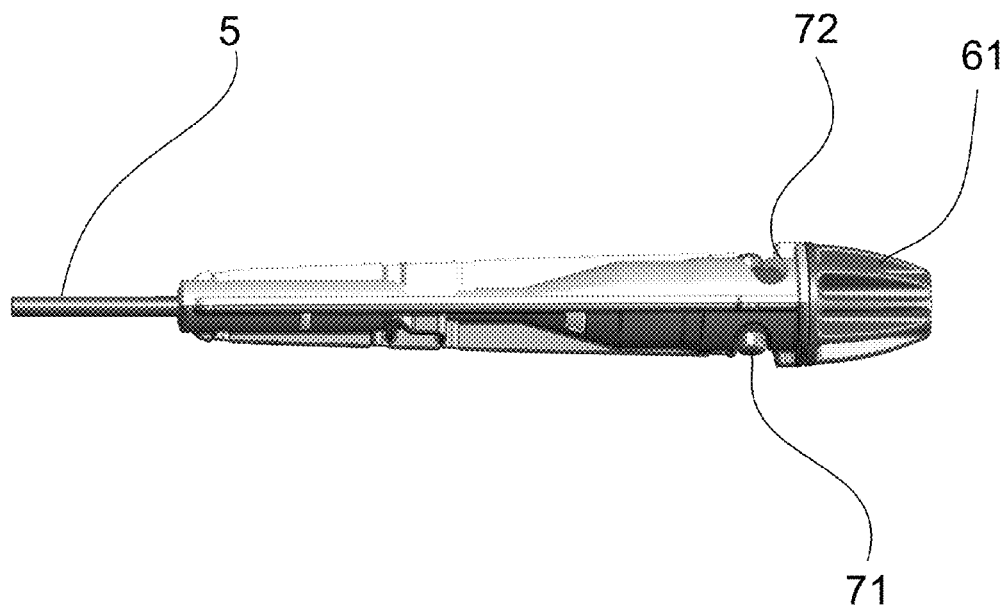
FIG. 9 is a schematic diagram showing a side view of the handle of FIG. 8.
Figure 10A:
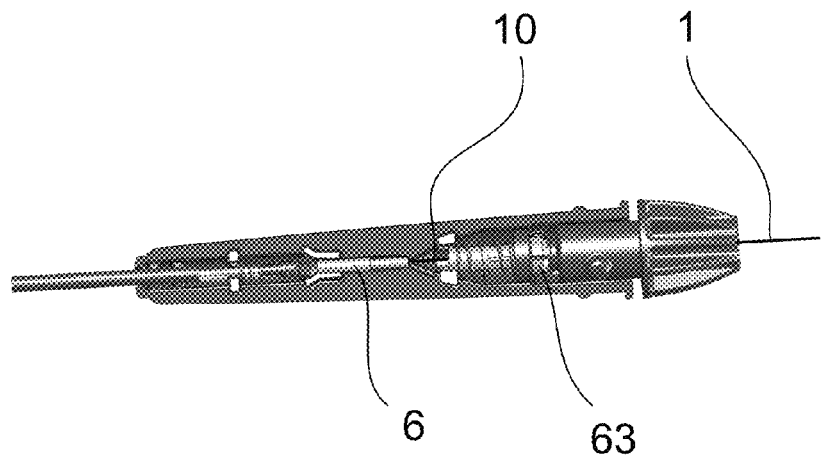
FIGS. 10a and 10b are schematic diagrams showing a cross-section view of the handle of FIG. 8 in the open position (FIG. 10a) and the closed position (FIG. 10b).
Figure 10B:
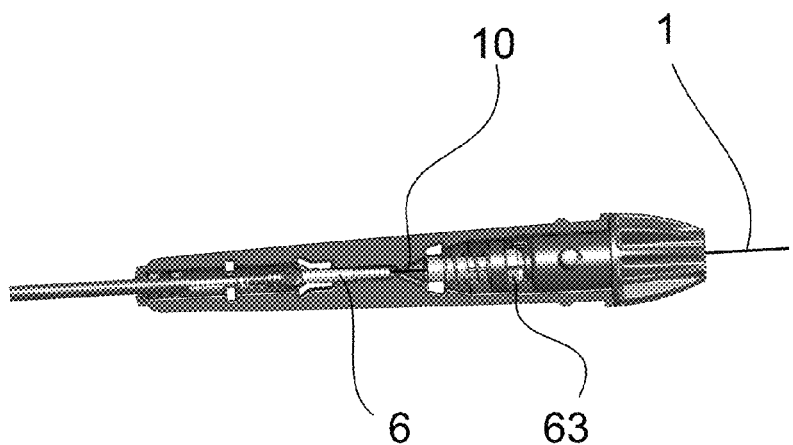

FIG. 10a shows the connector handle in an open position and FIG. 10b shows the connector handle in a closed (downward) position, where one can see the downward position in FIG. 10b of both the collet 63 and the female optical receiving device 6. The downward displacement of guidewire 1 pushing against female optical receiving device 6 is provided by the pitch of the sliding rail 72 and its interaction with protrusion 71 (see FIG. 9). The downward displacement of the guidewire 1 against the female optical receiving device 6 translates into contacting pressure between both optical termination interfaces (guidewire optical termination surface 31 (see FIG. 4) and the optical surface 56 of the second optical fiber 55 (see FIG. 7a). The force is provided by the spring 67 that is pushing against female optical receiving device 6. The spring 67, applies its pressure on the female optical receiving device 6 through a flange 69 that is mounted on the second ferrule 53 (see FIG. 7a). The pressure between the optical interfaces assures a good physical contact and therefore a good optical connection.

The above method of exerting a mutual pressure on the optical termination surfaces of both a guidewire and an optical receiving device is described by way of an example. Other methods of imposing a relative movement between the guidewire and the optical receiving device are understood to be within the scope of the present description. For example, there may exist a method for moving the internal receiving device apart from the guidewire prior to guidewire insertion, followed by a release after the guidewire is tightened within a connector handle.

The quality of the optical connection is related to the relative centering of both optical fiber axis where they interface. One method for reducing the tolerance on this centering is to use a second optical fiber 55 in the optical interface cable 5 with a core diameter different from the core diameter of the optical fiber (not shown) of the guidewire 1. Although this approach is not always possible, there are optical measuring methods that are well suited for such a strategy. For instance, the pressure sensor described in U.S. Pat. No. 7,689,071 and associated signal conditioning unit described in U.S. Pat. No. 7,259,862 are well suited for the implementation of such a strategy.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A method for terminating a first optical fiber within a proximal portion of a guidewire tubing, the guidewire tubing having an outside diameter, the outside diameter of the guidewire tubing being defined as having a tolerance of ±0.001" or less, the method comprising centering the first optical fiber relative to the outside diameter of the proximal portion of the guidewire tubing using an alignment centering tubing device which comprises a first ferrule having an inside diameter adapted to the outside diameter of the guidewire tubing, and a second ferrule having an inside diameter adapted to an outside diameter of the first optical fiber, the method further comprising concentrically aligning the first ferrule and the second ferrule.

2. The method of claim 1, further comprising grinding, polishing, or etching the guidewire tubing to bring the outside diameter within the tolerance of ±0.001" or better.

3. The method of claim 1, wherein a gap exists between an outside diameter of the first optical fiber and an inside diameter of the guidewire tubing, the method further comprising slipping an overlay tubing over the first optical fiber to fill the gap at least in part.

4. The method of claim 1, further comprising using an adhesive for securing the first optical fiber in the center of guidewire proximal portion.

5. The method of claim 4, wherein a gap exists between an outside diameter of the first optical fiber and an inside diameter of the guidewire tubing, and wherein the centering further comprising slipping an overlay tubing over the first optical fiber to fill the gap at least in part.

6. The method of claim 5, wherein using the alignment centering tubing device comprises using a first ferrule having an inside diameter adapted to the outside diameter of the guidewire tubing, and a second ferrule having an inside diameter adapted to an outside diameter of the overlay tubing.

7. The method of claim 1, wherein the aligning the first ferrule and second ferrule comprises using a split sleeve over the first ferrule and second ferrule thereby holding both ferrules coaxially.

8. A method for terminating a first optical fiber within a proximal portion of a guidewire tubing, the method comprising centering the first optical fiber relative to the outside diameter of the guidewire tubing, using an alignment centering tubing device which comprises a first ferrule having an inside diameter adapted to the outside diameter of the guidewire tubing, and a second ferrule having an inside diameter adapted to an outside diameter of the first optical fiber, the method further comprising concentrically aligning the first ferrule and the second ferrule and using an adhesive for securing the first optical fiber in the center of guidewire proximal portion.

9. The method of claim 8, wherein the aligning the first ferrule and second ferrule comprises using a split sleeve over the first ferrule and second ferrule thereby holding both ferrules coaxially.

* * * * *

UNITED STATES PATENT AND TRADEMARK OFFICE
CERTIFICATE OF CORRECTION

PATENT NO.       : 8,936,401 B2  
APPLICATION NO.  : 13/598596  
DATED            : January 20, 2015  
INVENTOR(S)      : Claude Belleville et al.

Page 1 of 1

It is certified that error appears in the above-identified patent and that said Letters Patent is hereby corrected as shown below:

On the Title Page  
In item no. 60 (Related U.S. Application Data)  
please change to:  
"Provisional application No. is 61/529,029, filed on Aug. 30, 2011."

Signed and Sealed this  
Seventh Day of July, 2015

Michelle K. Lee  
*Director of the United States Patent and Trademark Office*